US009345452B2

(12) United States Patent
Miyake (10) Patent No.: US 9,345,452 B2
(45) Date of Patent: *May 24, 2016

(54) ULTRASOUND OBSERVATION SYSTEM AND OPERATION METHOD OF ULTRASOUND OBSERVATION SYSTEM

(71) Applicant: OLYMPUS CORPORATION, Tokyo (JP)

(72) Inventor: Tatsuya Miyake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,103

(22) Filed: Jan. 7, 2015

(65) Prior Publication Data

US 2015/0126866 A1 May 7, 2015

Related U.S. Application Data

(63) Continuation of application No. PCT/JP2014/062101, filed on May 1, 2014.

(30) Foreign Application Priority Data

Jun. 26, 2013 (JP) .................................. 2013-133888

(51) Int. Cl.
*A61B 8/00* (2006.01)
*A61B 8/08* (2006.01)
(Continued)

(52) U.S. Cl.
CPC .............. *A61B 8/485* (2013.01); *A61B 5/0053* (2013.01); *A61B 5/0402* (2013.01); *A61B 8/02* (2013.01);
(Continued)

(58) Field of Classification Search
CPC ...... A61B 8/145; A61B 8/483; A61B 5/0048; A61B 5/0064; A61B 5/1127; A61B 8/08; A61B 8/485; A61B 2562/043; G01S 7/2033; G01S 15/8934; G01S 15/8979; G01S 15/8993
See application file for complete search history.

(56) References Cited

U.S. PATENT DOCUMENTS 6,014,473 A * 1/2000 Hossack ................ A61B 8/145
348/169
7,435,232 B2 * 10/2008 Liebschner .......... A61B 5/0048
128/920

(Continued)

FOREIGN PATENT DOCUMENTS

CN 201958909 U 9/2011
CN 102308207 A 1/2012

(Continued)

OTHER PUBLICATIONS

Extended Supplementary European Search Report dated Feb. 12, 2016 from related European Application No. 14 81 8059.9.

(Continued)

*Primary Examiner* — Joel Lamprecht
(74) *Attorney, Agent, or Firm* — Scully, Scott, Murphy & Presser, P.C.

(57) ABSTRACT

An ultrasound observation system includes: an ultrasound transducer that transmits ultrasound to a subject and receives ultrasound from the subject and generates an ultrasound signal; a displacement measurement circuit for elasticity image generation that measures a displacement of the subject based on the ultrasound signal; an elasticity modulus calculation circuit that calculates an elasticity modulus of the subject based on the measured displacement; a first automatic pressurization mechanism that generates a pressurization displacement in the subject; a signal waveform analysis circuit that analyzes a periodic motion based on a waveform of a signal that is based on a spontaneous displacement of the subject; and a pressurization mechanism control circuit that controls the first automatic pressurization mechanism so as to generate a pressurization displacement that reduces an influence of the spontaneous displacement of the subject at a time that an elasticity modulus is calculated based on the signal waveform analysis result.

16 Claims, 9 Drawing Sheets

(51) Int. Cl.
 A61B 8/12 (2006.01)
 A61B 5/0402 (2006.01)
 A61B 8/02 (2006.01)
 A61B 5/00 (2006.01)

(52) U.S. Cl.
 CPC . *A61B 8/12* (2013.01); *A61B 8/461* (2013.01); *A61B 8/488* (2013.01); *A61B 8/5223* (2013.01); *A61B 8/5284* (2013.01); *A61B 5/0051* (2013.01); *A61B 8/463* (2013.01); *A61B 8/467* (2013.01); *A61B 8/5276* (2013.01); *A61B 8/54* (2013.01); *A61B 8/543* (2013.01)

(56) References Cited

U.S. PATENT DOCUMENTS

| | | | |
|---|---|---|---|
| 2003/0171672 | A1 | 9/2003 | Varghese et al. |
| 2004/0167403 | A1 | 8/2004 | Nightingale et al. |
| 2007/0083116 | A1 | 4/2007 | Sato |
| 2008/0249408 | A1* | 10/2008 | Palmeri ............... A61B 8/08 600/438 |
| 2009/0216131 | A1* | 8/2009 | Chase ................ A61B 5/0048 600/476 |
| 2009/0306515 | A1 | 12/2009 | Matsumura et al. |
| 2010/0081935 | A1 | 4/2010 | Matsumura et al. |
| 2010/0312116 | A1 | 12/2010 | Pernot et al. |
| 2011/0015524 | A1 | 1/2011 | Suzuki et al. |
| 2011/0301468 | A1 | 12/2011 | Sandrin et al. |
| 2015/0018680 | A1* | 1/2015 | Miyake ............... A61B 8/5207 600/438 |

FOREIGN PATENT DOCUMENTS

| | | |
|---|---|---|
| JP | 2000-060853 A | 2/2000 |
| JP | 2006-230618 A | 9/2006 |
| JP | 2007-082725 A | 4/2007 |
| JP | 2010-082337 A | 4/2010 |
| JP | 2012-528614 A | 11/2012 |
| JP | 2012-249776 A | 12/2012 |
| WO | WO 2010/139519 A1 | 12/2010 |
| WO | WO 2011/034005 A1 | 3/2011 |

OTHER PUBLICATIONS

Tzschatzsch, H. et al., "In Vivo Time Harmonic Elastography of the Human Heart", Ultrasound in Medicine and Biology, Nov. 5, 2011, vol. 38, No. 2, pp. 214-222.

Tzschatzsch, H. et al., "Direct Elastography of in vivo human heart", Proc. International Society for Magnetic Resonance in Medicine, 19, Jan. 1, 2011, p. 275.

* cited by examiner

ULTRASOUND OBSERVATION SYSTEM AND OPERATION METHOD OF ULTRASOUND OBSERVATION SYSTEM

CROSS REFERENCE TO RELATED APPLICATION

This application is a continuation application of PCT/JP2014/062101 filed on May 1, 2014 and claims benefit of Japanese Application No. 2013-133888 filed in Japan on Jun. 26, 2013, the entire contents of which are incorporated herein by this reference.

BACKGROUND OF THE INVENTION

1. Field of the Invention

The present invention relates to an ultrasound observation system that generates an image based on an ultrasound signal that is obtained by transmitting and receiving ultrasound, and also to an operation method of the ultrasound observation system.

2. Description of the Related Art

Ultrasound diagnostic apparatuses that have an ultrasound endoscope and are equipped with an elastography function that displays the elasticity of tissue are in practical use. Such ultrasound diagnostic apparatuses are configured to generate an elasticity image (elastography mode image) that represents the rigidity or softness of living tissue based on the amount of strain in the living tissue that is generated by a pressing force.

An elasticity modulus for generating an elasticity image is determined based on a displacement amount of living tissue that is produced as a result of a surgeon pressing a probe against the living body or based on a displacement amount of living tissue that arises due to beating (pulsation).

On the other hand, in the case of displaying elasticity images utilizing an ultrasound endoscope, it is conceivable to utilize a displacement caused by beating (pulsation).

For example, in Japanese Patent Application Laid-Open Publication No. 2010-82337, technology for an ultrasound observation apparatus that displays the elasticity of living tissue is disclosed that presses living tissue by inserting a fluid into a balloon and withdrawing the fluid therefrom. At such case, a pressure sensor is provided that measures the pressure inside the balloon, and pressure transitions as well as the degree of expansion and contraction of the balloon are displayed on a monitor so that an examiner can visually ascertain such information. In addition, the aforementioned publication discloses an embodiment that, in a case where an appropriate amount of pressing with respect to the living tissue of a subject cannot be obtained only by inserting and withdrawing fluid by manual operation of a lever by the examiner, supports the performance of an appropriate pressing operation by using a control adjustment portion that inserts and withdraws fluid in an auxiliary manner.

Further, Japanese Patent Application Laid-Open Publication No. 2006-230618 discloses technology for an ultrasound observation apparatus that measures properties such as the elasticity of tissue which, to enable stable measurement even in the case of tissue that periodically changes shape, such as the heart, varies the gain of an ultrasound signal in synchrony with a heartbeat cycle that is measured by an electrocardiograph or the like, and thus suppresses the occurrence of a situation in which the reception level fluctuates accompanying changes in tissue shape. Further, as another embodiment in the aforementioned publication; technology is disclosed that uses an excitation apparatus to periodically change the shape of a static organ that does not actively change shape, and measures the elasticity thereof.

In addition, International Publication No. WO 2011/034005 discloses technology that, in an ultrasound observation apparatus that displays the elasticity of tissue, extracts and displays an image of tissue in an appropriate pressed state based on displacement data, elasticity data, an electrocardiographic waveform or the like.

SUMMARY OF THE INVENTION

An ultrasound observation system according to a certain aspect of the present invention includes: an ultrasound transducer that transmits ultrasound to a subject, receives the ultrasound that is reflected by the subject, and generates an ultrasound signal based on the ultrasound that is received; a displacement measurement portion that measures a displacement of the subject based on the ultrasound signal, in order to generate an elasticity image of the subject; an elasticity modulus calculation portion that calculates an elasticity modulus of the subject based on a measurement result of the displacement measurement portion; a pressurization portion that applies a pressing force to the subject to generate a pressurization displacement; a signal waveform analysis portion that analyzes a periodic motion of the subject based on a waveform of a signal that is based on a spontaneous displacement of the subject; and a pressurization control portion that, based on the periodic motion of the subject that is analyzed by the signal waveform analysis portion, controls the pressurization portion so that the pressurization portion applies a pressing force to the subject and generates the pressurization displacement so as to reduce an influence of the spontaneous displacement of the subject at a time that the elasticity modulus is calculated by the elasticity modulus calculation portion.

An operation method of an ultrasound observation system according to a certain aspect of the present invention is an operation method in which: an ultrasound transducer transmits ultrasound to a subject, receives the ultrasound that is reflected by the subject, and generates an ultrasound signal based on the ultrasound that is received; a displacement measurement portion measures a displacement of the subject based on the ultrasound signal, in order to generate an elasticity image of the subject; an elasticity modulus calculation portion calculates an elasticity modulus of the subject based on a measurement result of the displacement measurement portion; a pressurization portion applies a pressing force to the subject to generate a pressurization displacement; a signal waveform analysis portion analyzes a periodic motion of the subject based on a waveform of a signal that is based on a spontaneous displacement of the subject; and, based on the periodic motion of the subject that is analyzed by the signal waveform analysis portion, a pressurization control portion controls the pressurization portion so that the pressurization portion applies a pressing force to the subject and generates the pressurization displacement so as to reduce an influence of the spontaneous displacement of the subject at a time that the elasticity modulus is calculated by the elasticity modulus calculation portion.

DETAILED DESCRIPTION OF THE PREFERRED EMBODIMENTS

Hereunder, embodiments of the present invention are described with reference to the accompanying drawings.

[Embodiment 1]

Figure 1:
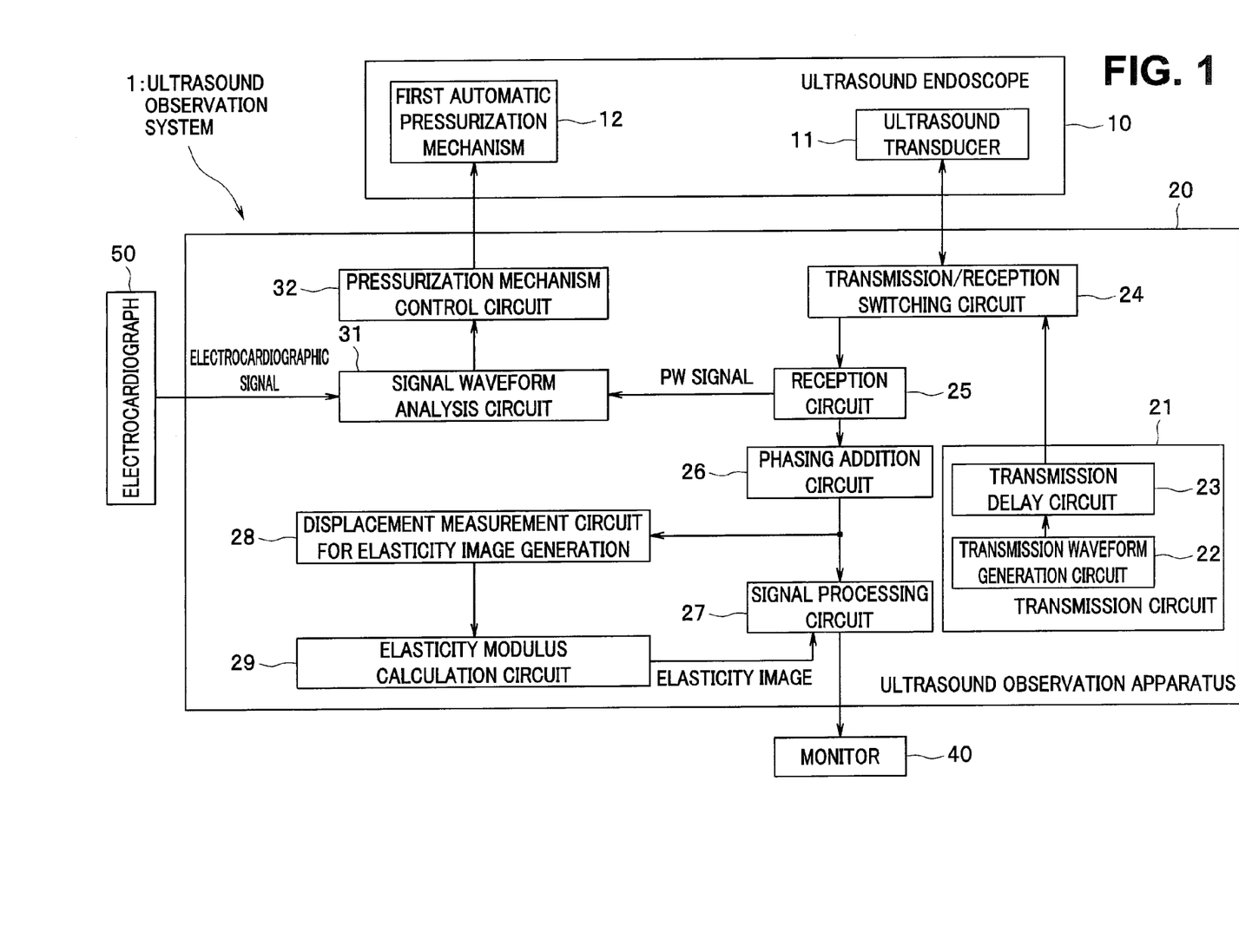
FIG. 1 is a block diagram illustrating the configuration of an ultrasound observation system in Embodiment 1 of the present invention.

FIG. 1 to FIG. 7 illustrate Embodiment 1 of the present invention, among which FIG. 1 is a block diagram that illustrates the configuration of an ultrasound observation system 1.

FIG. 1 illustrates the configuration of the ultrasound observation system 1 into which, for example, an electrocardiographic signal is inputted from an electrocardiograph 50. However, the electrocardiograph 50 is not essential, and as described hereunder, it is also possible to use a pulse-wave Doppler signal (hereunder, referred to as a "PW signal") from a reception circuit 25 instead of an electrocardiographic signal from the electrocardiograph 50.

The ultrasound observation system 1 is a system that transmits ultrasound to a subject, receives the ultrasound that was reflected by the subject, and generates an image based on an ultrasound signal that is obtained based on the received ultrasound. The ultrasound observation system 1 includes an ultrasound endoscope 10, an ultrasound observation apparatus 20, and a monitor 40.

The ultrasound endoscope 10 is a probe that includes an ultrasound transducer 11 and a first automatic pressurization mechanism 12. Note that although the ultrasound endoscope 10 used in this case is of a type that is inserted into the body, the ultrasound observation system 1 may also be constructed using an extracorporeal ultrasound probe.

The ultrasound transducer 11 transmits ultrasound to a subject, receives the ultrasound that was reflected by the subject, and generates an ultrasound signal based on the received ultrasound. For example, the ultrasound transducer 11 is constructed as a transducer array in which a large number of transducers are arrayed.

The first automatic pressurization mechanism 12 is a pressurization portion that applies a pressing force to a subject at a timing that is based on a trigger signal from a pressurization mechanism control circuit 32, described later, to thereby generate a pressurization displacement. The first automatic pressurization mechanism 12 may have a configuration such that, for example, fluid (a liquid is preferable if ensuring that ultrasound transmitted and received by the ultrasound transducer 11 is not attenuated is to be taken into consideration) is inserted into and withdrawn from a balloon to cause the balloon surface that serves as a pressurization face that comes in contact with a subject to oscillate; or may have a configuration that uses a driving source such as a motor to cause a pressurization face that comes in contact with a subject to oscillate, or another configuration may also be adopted.

The ultrasound observation apparatus 20 includes a transmission circuit 21, a transmission/reception switching circuit 24, a reception circuit 25, a phasing addition circuit 26, a signal processing circuit 27, a displacement measurement circuit for elasticity image generation 28, an elasticity modulus calculation circuit 29, a signal waveform analysis circuit 31, and a pressurization mechanism control circuit 32.

The transmission circuit 21 includes a transmission waveform generation circuit 22 and a transmission delay circuit 23.

The transmission waveform generation circuit 22 generates and outputs a signal waveform for driving each transducer constituting the ultrasound transducer 11.

The transmission delay circuit 23 regulates the drive timing of each transducer constituting the ultrasound transducer 11. By this means, the focal point and direction of an ultrasound beam transmitted from the ultrasound transducer 11 is controlled, and the ultrasound can be converged at a desired position (depth).

The transmission/reception switching circuit 24, for example, includes a multiplexer that sequentially selects a plurality of transducers for performing transmission and reception of ultrasound waves, and transmits a driving signal from the transmission circuit 21 to the ultrasound transducer 11, and also transmits an ultrasound signal (echo signal) from the ultrasound transducer 11 to the reception circuit 25.

The reception circuit 25 receives the ultrasound signal from the transmission/reception switching circuit 24, and subjects the ultrasound signal to processing such as amplification or conversion to a digital signal.

The phasing addition circuit 26 delays ultrasound signals to adjust the phases, and thereafter adds the phases.

In an ultrasound diagnosis mode, the signal processing circuit 27 performs coordinate conversion and interpolation processing on the ultrasound signal from the phasing addition circuit 26 to create an ultrasound image as an image for display. In addition, in an elasticity image observation mode, the signal processing circuit 27 creates an elasticity image from the elasticity modulus calculation circuit 29 as an image for display, or superimposes an elasticity image on an ultrasound image to create an image for display.

The displacement measurement circuit for elasticity image generation 28 is a displacement measurement portion that measures a displacement amount for an image of a subject (displacement amount for generating an elasticity image of a subject) based on an ultrasound signal.

The elasticity modulus calculation circuit 29 is an elasticity modulus calculation portion that calculates an elasticity modulus of a subject based on the displacement amount for an image that was measured by the displacement measurement circuit for elasticity image generation 28. In order to calculate an elasticity modulus for each coordinate of the subject, the calculation result of the elasticity modulus calculation circuit 29 is an elasticity image in which the elasticity modulus is distributed on two-dimensional coordinates.

The signal waveform analysis circuit 31 is a signal waveform analysis portion that analyzes a signal that is based on a displacement of the subject (for example, an electrocardiographic signal from the electrocardiograph 50, or a PW signal from the reception circuit 25), and analyzes a periodic motion of the subject. Specifically, the signal waveform analysis circuit 31 acquires an analysis result that includes a local maximum point of a displacement of the subject that is based on a spontaneous displacement as well as a displacement cycle (that is, further analysis may also be performed to also acquire other information as the analysis result).

The pressurization mechanism control circuit 32 is a pressurization control portion that, based on the analysis result of the signal waveform analysis circuit 31, controls so as to cause the first automatic pressurization mechanism 12 to perform pressurization for reducing the influence of a motion of the subject on the elasticity modulus calculation result in accordance with the periodic motion of the subject. Based on the analysis result of the signal waveform analysis circuit 31, the pressurization mechanism control circuit 32 controls so as to cause the first automatic pressurization mechanism 12 to perform pressurization at a timing that corresponds with the local maximum point of the displacement (for example, the same timing as the local maximum point of the displacement (preferably, the maximum point among local maximum points within a single cycle)), in synchrony with the acquired displacement cycle. Specifically, based on a timing at which a displacement amount that is based on a spontaneous displacement of the subject becomes equal to or greater than a previously set threshold value Th (see FIG. 4, FIG. 5 and the like), the pressurization mechanism control circuit 32 generates a trigger signal tr1 (see FIG. 4, FIG. 5 and the like) such that the first automatic pressurization mechanism 12 performs pressurization at the same timing as the local maximum point of the displacement, and outputs the generated trigger signal tr1 to the first automatic pressurization mechanism 12. Note that although in the present embodiment the first automatic pressurization mechanism 12 is caused to perform pressurization at the same timing as a local maximum point of the displacement of the subject, since an effect can be obtained to a certain degree even if the first automatic pressurization mechanism 12 is caused to perform pressurization at a timing that deviates a little from the local maximum point, the present invention is not limited to causing pressurization to be performed at the same timing as the local maximum point.

The monitor 40 displays an image for display that is received from the signal processing circuit 27.

Figure 2:
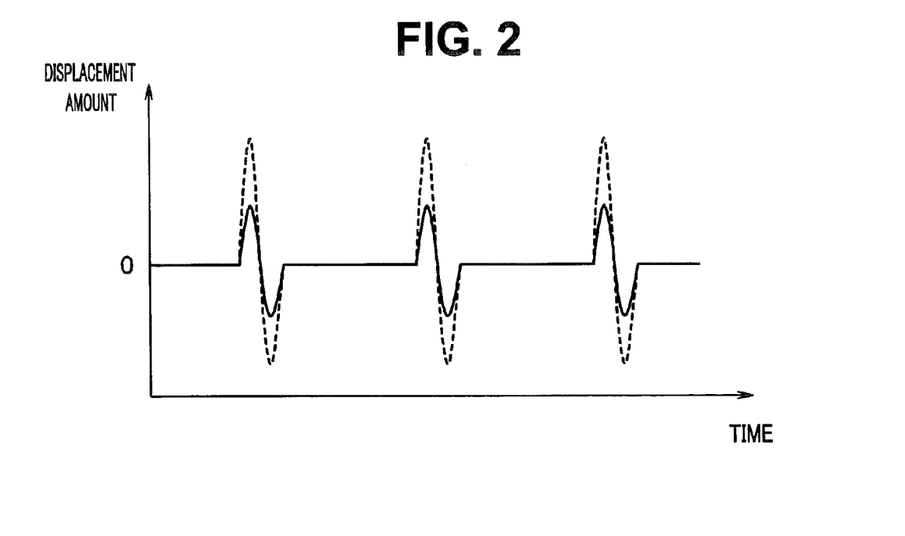
FIG. 2 is a diagram illustrating an example of changes over time in a displacement amount when automatic pressurization was performed in synchrony with a spontaneous displacement of a subject in the aforementioned Embodiment 1.

FIG. 2 is a diagram illustrating an example of changes over time in a displacement amount when automatic pressurization was performed in synchrony with a spontaneous displacement of the subject.

In FIG. 2, a solid line shows changes over time in a displacement amount caused by a spontaneous displacement of the subject (for example, a displacement amount caused by only beating or pulsation of the subject).

Further, a dashed line shows changes over time in a displacement amount of the subject when a pressurization displacement amount that is produced by automatic pressurization is added to the spontaneous displacement amount of the subject that is shown by the solid line (accordingly, the displacement amount shown by the dashed line includes both the spontaneous displacement amount and the pressurization displacement amount). As described above, pressurization from the first automatic pressurization mechanism 12 is performed so as to be, for example, at the same timing as the local maximum point of the spontaneous displacement of the subject.

Figure 3:
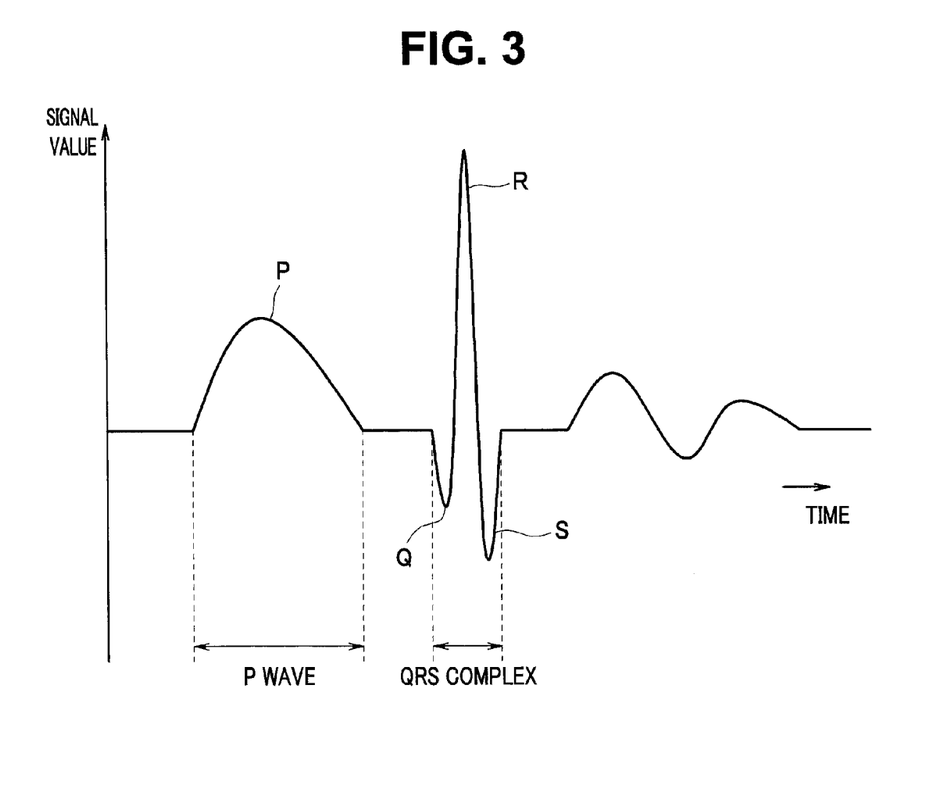
FIG. 3 is a diagram illustrating an example of an electrocardiographic signal that is detected by an electrocardiograph in the aforementioned Embodiment 1.

FIG. 3 is a diagram that illustrates an example of an electrocardiographic signal detected by the electrocardiograph 50.

Waveforms that are obtained as electrocardiographic signals include a P wave that is considered to be a waveform that reflects electric excitation of the atrium, and a QRS complex that is considered to include waveforms that reflect electric excitation of the ventricle. However, the waveforms are not limited thereto, and other examples include a T wave and a U wave. The wave with the largest amplitude among these waves is the R wave among the Q wave, R wave, and S wave that constitute the QRS complex. The crest of the R wave provides the local maximum point of the spontaneous displacement of the subject (in particular, the maximum point within a single cycle). Therefore, since it is considered logical to utilize the R wave with respect to the displacement for generating an elasticity image, in the present embodiment a configuration is adopted that applies a pressurization displacement in synchrony with the R wave (however, the present invention is not limited to the R wave).

Figure 4:
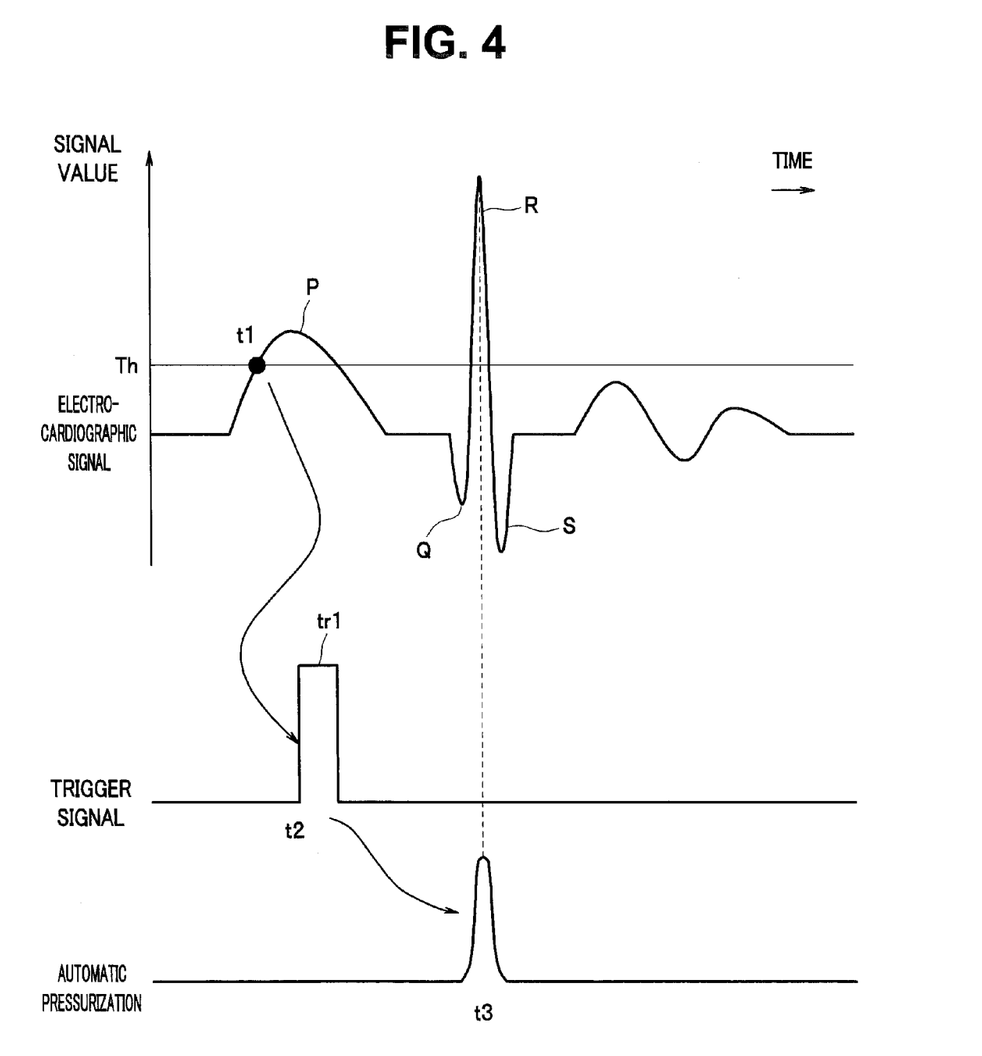
FIG. 4 is a diagram illustrating an example in which a trigger signal is generated at a timing that is based on a detected electrocardiographic signal to perform automatic pressurization in synchrony with a spontaneous displacement of the subject in the aforementioned Embodiment 1.

As shown in FIG. 3, the P wave is a wave that is obtained temporally prior to the QRS complex that includes the R wave. Therefore, for example, it is conceivable to generate a trigger signal at a timing as shown in FIG. 4 to perform automatic pressurization. FIG. 4 is a diagram that illustrates an example of generating the trigger signal tr1 at a timing that is based on a detected electrocardiographic signal, and performing automatic pressurization in synchrony with a spontaneous displacement of the subject.

That is, a timing t1 at which the P wave that is prior to the R wave becomes equal to or greater than the predetermined threshold value Th is measured. If the displacement cycle is already acquired, a timing t3 at which the R wave occurs can be estimated based on the timing t1. Accordingly, the pressurization mechanism control circuit 32 generates the trigger signal tr1 and applies the trigger signal tr1 to the first automatic pressurization mechanism 12 at a timing t2 so that the timing at which pressurization from the first automatic pressurization mechanism 12 is performed is the estimated timing t3.

By this means, automatic pressurization by the first automatic pressurization mechanism 12 is performed at the timing t3, and a displacement caused by the automatic pressurization is superposed on a displacement caused by the R wave (see FIG. 2).

Note that, because the amplitude of a T wave is comparatively large (for example, larger than that of a P wave), a timing at which an R wave occurs can also be estimated based on a T wave instead of a P wave. In a case where the R-wave period is stable, a configuration may be adopted so as to estimate the timing at which the next R wave will occur based on the timing at which the previous R wave was generated. Other estimation methods may also be used.

Figure 5:
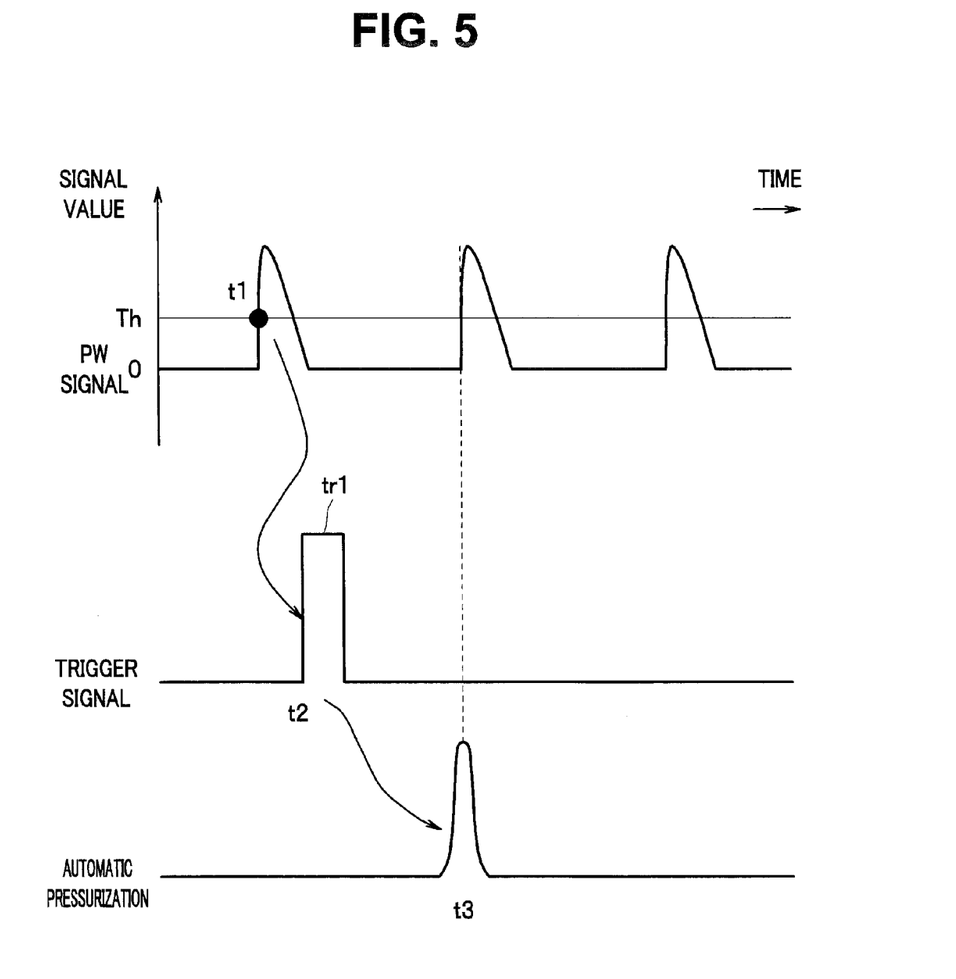
FIG. 5 is a diagram illustrating an example in which a trigger signal is generated at a timing that is based on a detected PW signal to perform automatic pressurization in synchrony with a spontaneous displacement of the subject in the aforementioned Embodiment 1.

On the other hand, FIG. 5 is a diagram that illustrates an example of generating a trigger signal at a timing that is based on a detected PW signal, and performing automatic pressurization in synchrony with a spontaneous displacement of the subject.

Naturally, detection of a spontaneous displacement of the subject is not limited to detection by means of an electrocardiographic signal from the electrocardiograph 50. For example, a spontaneous displacement can also be detected by means of a PW signal from the reception circuit 25. For example, it is assumed that a signal waveform shown in FIG. 5 was obtained as the PW signal.

In this case also, similarly to the case of the electrocardiographic signal, a timing t1 at which the signal value of the PW signal becomes equal to or greater than a predetermined threshold value Th is measured (however, the threshold value Th is a value that is defined in accordance with the PW signal, and in general is different from the value of the threshold value Th used in the case of the electrocardiographic signal).

If the displacement cycle is already acquired, a timing t3 at which a spontaneous displacement of the subject will next occur (that is, a timing at which the signal value of the PW signal will next become equal to or greater than the predetermined threshold value Th) can be estimated based on the timing t1, and similarly to the case described above, the pressurization mechanism control circuit 32 generates the trigger signal tr1 and applies the trigger signal tr1 to the first automatic pressurization mechanism 12 at a timing t2 so that the timing at which pressurization from the first automatic pressurization mechanism 12 is performed is the estimated timing t3.

Note that, although an electrocardiographic signal and a PW signal are mentioned as examples of a "signal that is based on a displacement of the subject" in the foregoing description, the present invention is not limited to these signals, and for example a configuration may also be adopted so as to generate a trigger signal based on a displacement amount for an image that is measured by the displacement measurement circuit for elasticity image generation 28 and to perform automatic pressurization based thereon, or that performs automatic pressurization based on a different signal.

Figure 6:
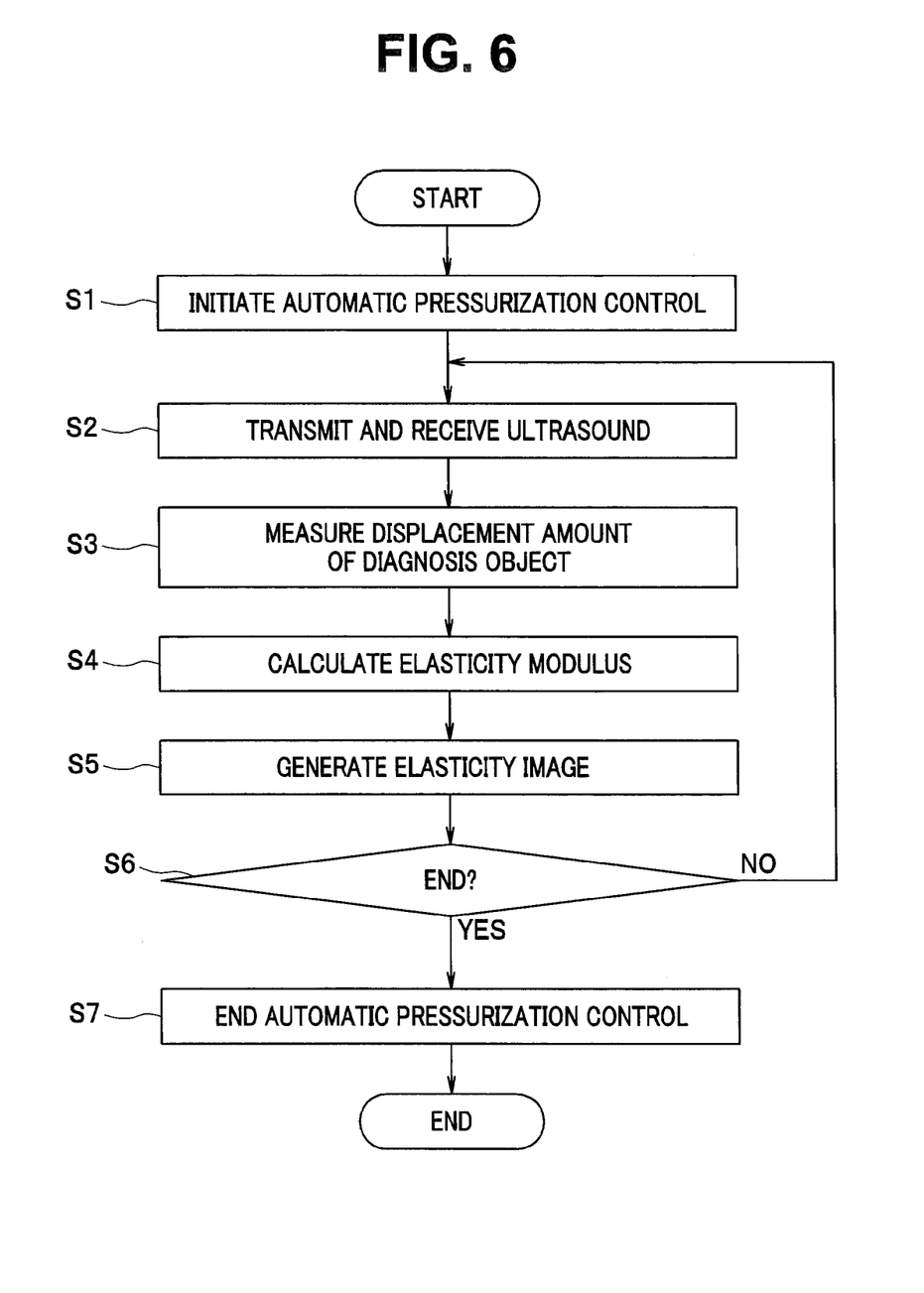
FIG. 6 is a flowchart illustrating elasticity image generation processing in the aforementioned Embodiment 1.

FIG. 6 is a flowchart that illustrates elasticity image generation processing.

The processing illustrated in FIG. 6 is started when the ultrasound observation system 1 is set to the elasticity image observation mode.

Figure 7:
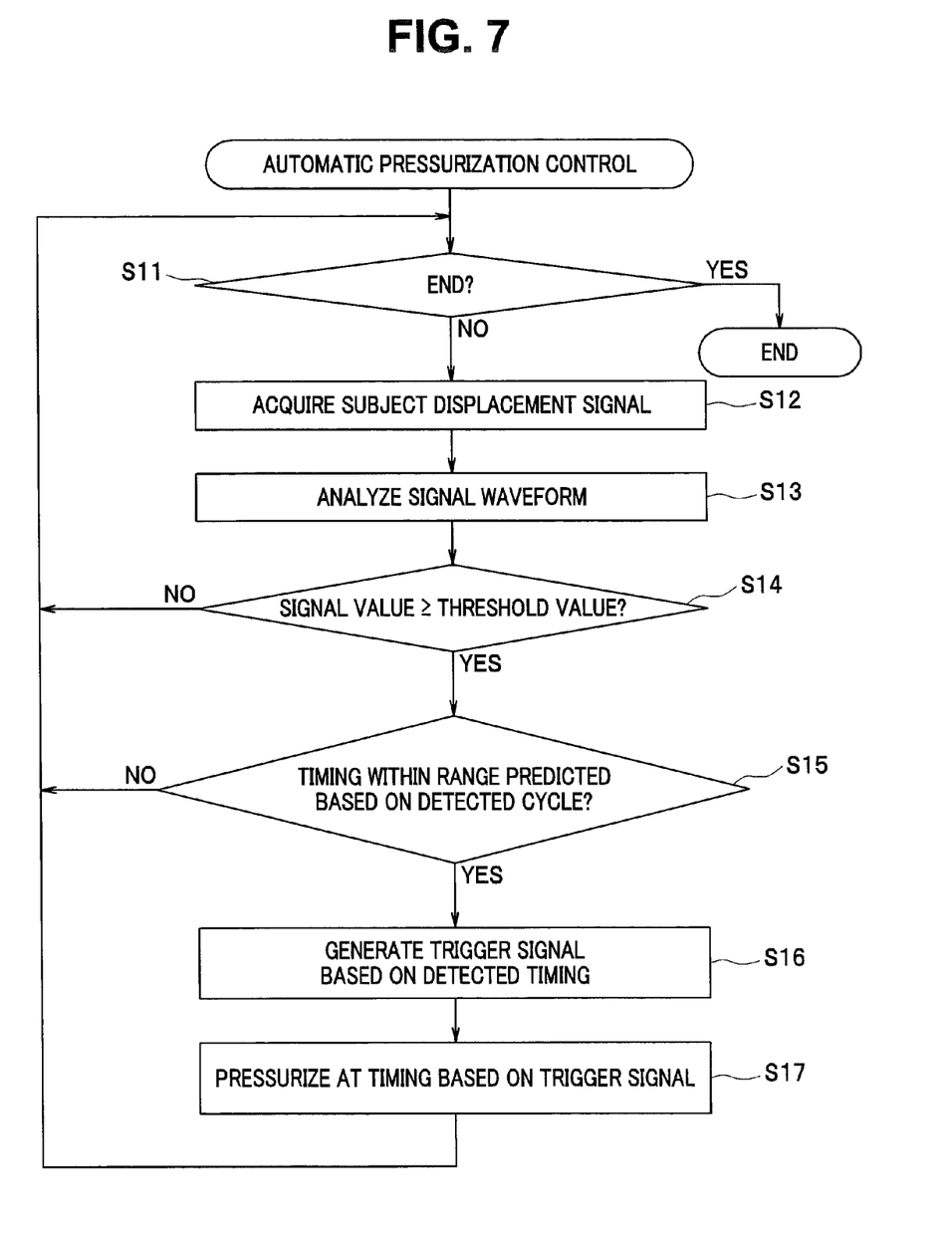
FIG. 7 is a flowchart illustrating processing for automatic pressurization control in the aforementioned Embodiment 1.

First, automatic pressurization control processing that is illustrated in FIG. 7 is initiated (step S1).

Subsequently, transmission and reception of ultrasound to and from the ultrasound transducer 11 is performed (step S2), and a displacement amount (displacement amount for an image) of the subject that is the diagnosis object is measured by the displacement measurement circuit for elasticity image generation 28 (step S3).

Next, based on the displacement amount for an image that was measured in step S3, the elasticity modulus calculation circuit 29 calculates an elasticity modulus of the subject for each coordinate of the subject (step S4).

The calculated elasticity moduli are sent to the signal processing circuit 27 together with the corresponding coordinates, and are used to generate an elasticity image for display (step S5). The elasticity image is, as necessary, further superimposed on an ultrasound image to create an image for display, and displayed on the monitor 40.

Thereafter, it is determined whether or not to end the processing (step S6). If the processing is not to be ended yet, the operation returns to step S2 to repeat the above described processing in order to generate an elasticity image of the next frame.

In contrast, if it is determined that the processing is to be ended, a termination signal is sent to the automatic pressurization control processing illustrated in FIG. 7, and thereafter the processing is ended (step S7), to thereby end the elasticity image generation processing.

FIG. 7 is a flowchart that illustrates processing of the automatic pressurization control.

When this automatic pressurization control processing is initiated in the above described step S1, first, it is determined whether or not to end the automatic pressurization control processing (step S11).

If it is determined in step S11 that the processing is not to end yet, the signal waveform analysis circuit 31 acquires, for example, an electrocardiographic signal or a PW signal as a signal that is based on a displacement of the subject (step S12).

Next, the signal waveform analysis circuit 31 performs analysis of the acquired electrocardiographic signal or PW signal, and acquires an analysis result that includes a local maximum point of the displacement and a displacement cycle (step S13).

The signal waveform analysis circuit 31 determines whether or not the electrocardiographic signal or PW signal is equal to or greater than the predetermined threshold value Th (step S14).

If it is determined in step S14 that the electrocardiographic signal or PW signal is equal to or greater than the predetermined threshold value Th, the signal waveform analysis circuit 31 further determines whether or not a timing at which the electrocardiographic signal or PW signal became equal to or greater than the predetermined threshold value Th is a timing within a range that is considered appropriate based on the acquired displacement cycle, that is, whether or not there is an erroneous detection based on noise or the like (step S15).

Here, if the timing is within a predicted range, the signal waveform analysis circuit 31 notifies the pressurization mechanism control circuit 32 to the effect that a timing (see the timing t1 in FIG. 4 or FIG. 5) at which the electrocardiographic signal or PW signal became equal to or greater than the predetermined threshold value Th was detected.

The pressurization mechanism control circuit 32 generates the trigger signal tr1 based on the timing t1 detected by the signal waveform analysis circuit 31, and applies the trigger signal tr1 to the first automatic pressurization mechanism 12 at the timing t2 shown in FIG. 4 or FIG. 5 (step S16).

The first automatic pressurization mechanism 12 receives the trigger signal tr1, and performs automatic pressurization with respect to the subject to cause a displacement of the subject at the timing t3 shown in FIG. 4 or FIG. 5 (step S17).

After the processing in step S17 has been performed as described above, or if the electrocardiographic signal or PW signal is not equal to or greater than the predetermined threshold value Th in step S14, or if the timing is not within the predicted range in step S15, the operation returns to the processing described in the foregoing step S11 to repeat the above described processing.

Thereafter, in step S11, in a case where a termination signal has been received from the processing in the above described step S7, the present automatic pressurization control processing is ended.

According to Embodiment 1 that is described above, a configuration is adopted in which the waveform of a signal that is based on a displacement of a subject is analyzed, a periodic motion of the subject is analyzed and, based on the analysis results, the first automatic pressurization mechanism 12 is caused to perform pressurization in accordance with the periodic motion of the subject. Hence, the influence of a motion of the subject on results of calculating the elasticity modulus can be reduced, and more stable elasticity images that take into account a displacement of the subject can be obtained.

At such time, by acquiring an analysis result that includes a local maximum point of the displacement and the displacement cycle, and causing the first automatic pressurization mechanism 12 to perform pressurization at a timing that corresponds with the local maximum point of the displacement in synchrony with the displacement cycle, a spontaneous displacement of the subject can be effectively utilized, and it is possible to decrease a pressurization displacement that is generated at the time of automatic pressurization.

In addition, at this time, since a configuration is adopted so as to automatically pressurize at the same timing as the local maximum point of the displacement, effective utilization of a spontaneous displacement of the subject can be optimized.

At such time, when using an electrocardiographic signal as the signal that is based on a displacement of the subject, a displacement of the heart can be directly and accurately acquired.

Further, when using a PW signal as the signal that is based on a displacement of the subject, it is not necessary to connect the external electrocardiograph 50 to the ultrasound observation apparatus 20, and thus the advance preparations can be simplified.

[Embodiment 2]

Figure 8:
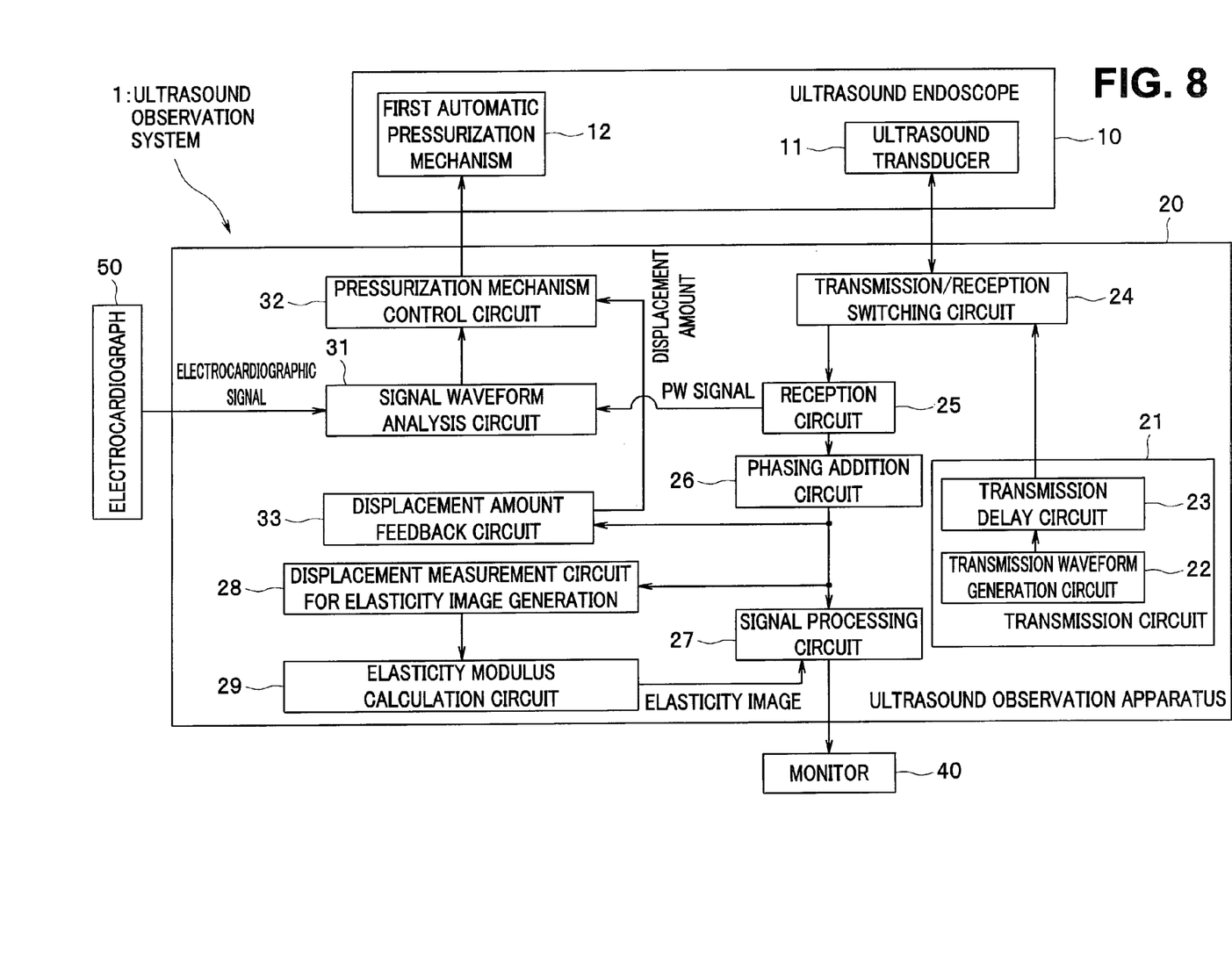
FIG. 8 is a block diagram illustrating the configuration of an ultrasound observation system in Embodiment 2 of the present invention.

FIG. 8 is a block diagram illustrating Embodiment 2 of the present invention, and illustrates the configuration of an ultrasound observation system 1.

In Embodiment 2, portions that are the same as in the foregoing Embodiment 1 are denoted by the same reference numerals and a description thereof is omitted as appropriate, and mainly only differences relative to the foregoing Embodiment 1 are described.

The ultrasound observation system 1 of the present embodiment has a configuration in which a displacement amount feedback circuit 33 is added to the configuration of the ultrasound observation apparatus 20 of the ultrasound observation system 1 of Embodiment 1 that is described above, and is configured so that the amplitude of the automatic pressurization (intensity of pressurization) is also controlled, and not just the timing at which to apply the automatic pressurization.

That is, in the ultrasound observation apparatus 20, the displacement amount feedback circuit 33 that calculates and outputs a displacement amount of the subject based on an ultrasound signal from the phasing addition circuit 26 is provided as a displacement amount feedback portion. The displacement amount feedback circuit 33 measures a displacement amount that is obtained by adding a spontaneous displacement and a pressurization displacement, such as is shown by the dashed line in FIG. 2, as a displacement amount of the subject, and feeds back the measured displacement amount to the pressurization mechanism control circuit 32.

The pressurization mechanism control circuit 32 determines a timing at which to cause the first automatic pressurization mechanism 12 to perform pressurization based on the analysis result of the signal waveform analysis circuit 31, and based on the displacement amount that is fed back from the displacement amount feedback circuit 33, also controls a pressurization displacement amount applied to the subject by the first automatic pressurization mechanism 12 so that the displacement amount maintains a constant value.

In this case, for example, automatic control so that a displacement amount that is obtained from the displacement amount feedback circuit 33 approaches a target displacement amount may be mentioned as the control that is performed by the pressurization mechanism control circuit 32 so that the displacement amount maintains a constant value. In this case, the pressurization mechanism control circuit 32 may previously store the target displacement amount therein, or a configuration may be adopted so that the target displacement amount can be set to a desired value by an input operation from outside.

Alternatively, automatic control may be performed so as to approach a displacement amount that was obtained the previous time from the displacement amount feedback circuit 33.

Thus, the first automatic pressurization mechanism 12 performs automatic pressurization while controlling the voltage applied to the circuit or the like so that the displacement amount maintains a constant value.

According to Embodiment 2, in addition to obtaining substantially the same advantageous effects as in the above described Embodiment 1, since the displacement amount of the subject is also controlled so as to be constant, elasticity images having increased stability can be obtained.

[Embodiment 3]

Figure 9:
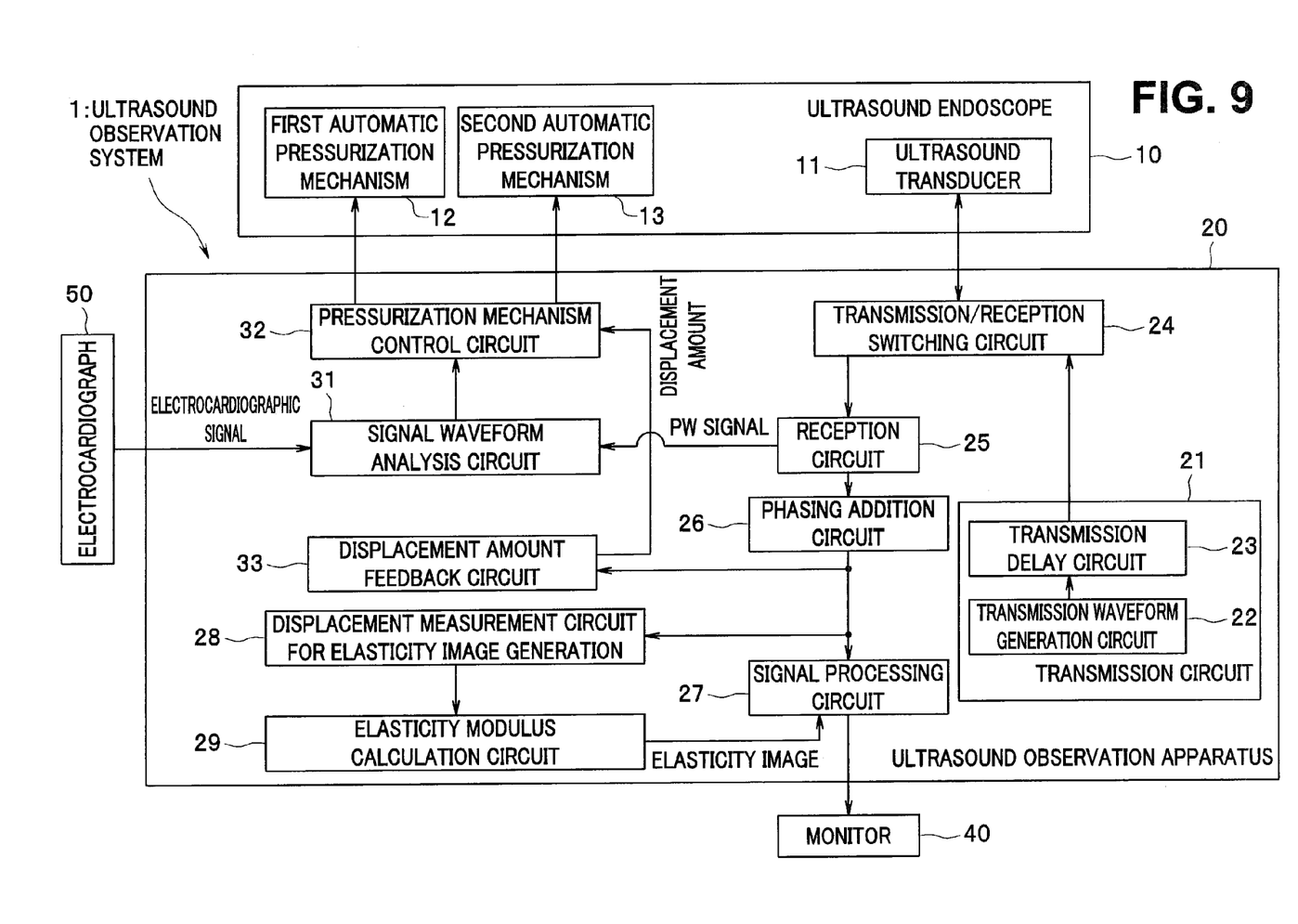
FIG. 9 is a block diagram illustrating the configuration of an ultrasound observation system in Embodiment 3 of the present invention.
Figure 10:
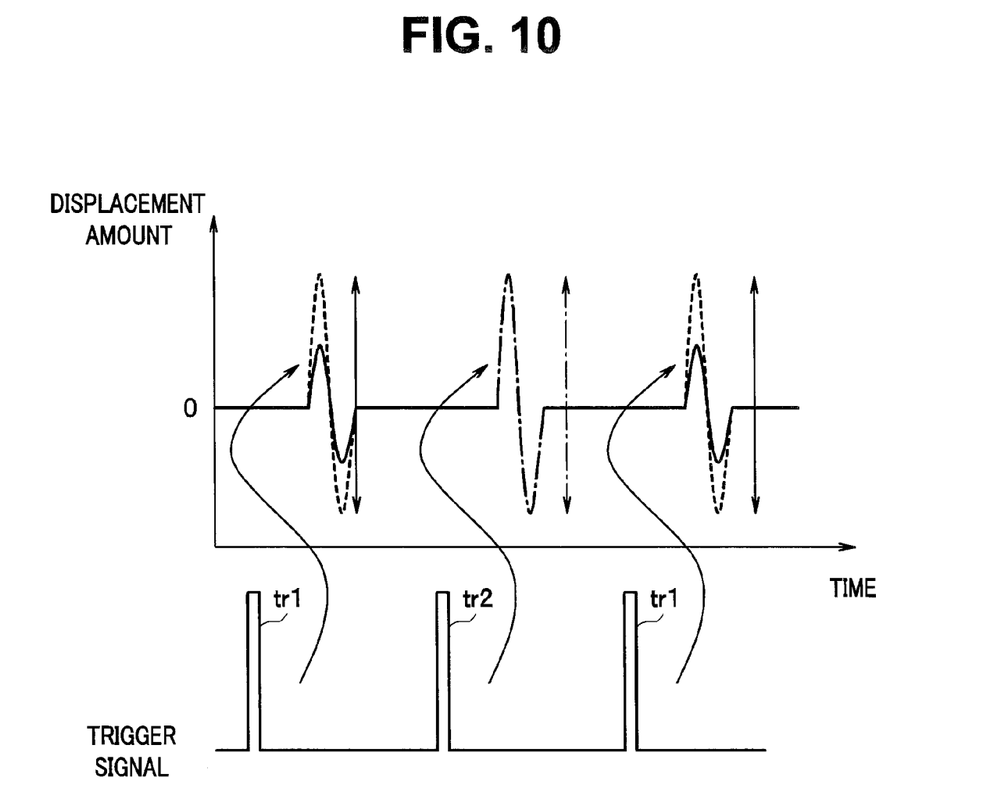
FIG. 10 is a diagram illustrating an example of changes over time in a trigger signal and a displacement amount when, in the aforementioned Embodiment 3, automatic pressurization is performed in synchrony with a spontaneous displacement of a subject and, in addition, automatic pressurization is also performed during a period between successive spontaneous displacements.

FIG. 9 and FIG. 10 are diagrams that illustrate Embodiment 3 of the present invention. FIG. 9 is a block diagram illustrating the configuration of an ultrasound observation system 1. FIG. 10 is a diagram illustrating an example of changes over time in a trigger signal and a displacement amount when automatic pressurization is performed in synchrony with a spontaneous displacement of a subject and, in addition, automatic pressurization is also performed during a period between successive spontaneous displacements.

In Embodiment 3, portions that are the same as in the foregoing Embodiments 1 and 2 are denoted by the same reference numerals and a description thereof is omitted as appropriate, and mainly only differences relative to the foregoing Embodiments 1 and 2 are described.

The ultrasound observation system 1 of the present embodiment has a configuration in which a second automatic pressurization mechanism 13 is added to the configuration of the ultrasound endoscope 10 of the ultrasound observation system 1 of Embodiment 2 that is described above, and is configured so that automatic pressurization is not just performed at a timing that is synchronized with a spontaneous displacement of the subject, but is also performed during a period between successive spontaneous displacements of the subject.

That is, the ultrasound endoscope 10 includes the ultrasound transducer 11 and the first automatic pressurization mechanism 12 that is a first pressurization portion, and also includes a second automatic pressurization mechanism 13 that is a second pressurization portion. The second automatic pressurization mechanism 13 is a mechanism that performs automatic pressurization during a period between successive spontaneous displacements of the subject.

Note that, although in FIG. 9 the first automatic pressurization mechanism 12 and the second automatic pressurization mechanism 13 are illustrated as separate components, in the actual configuration, naturally a single automatic pressurization mechanism may serve as both the first automatic pressurization mechanism 12 and the second automatic pressurization mechanism 13.

Based on the analysis result of the signal waveform analysis circuit 31, the pressurization mechanism control circuit 32 generates a first trigger signal tr1 for causing the first automatic pressurization mechanism 12 to perform pressurization at, for example, the same timing as a local maximum point of the spontaneous displacement of the subject, and a second trigger signal tr2 for causing the second automatic pressurization mechanism 13 to perform pressurization at a timing that is between local maximum points of two successive spontaneous displacements of the subject, as shown in FIG. 10.

In this case, from the viewpoint that elasticity images can be acquired at equal time intervals, preferably a timing at which the second automatic pressurization mechanism 13 performs automatic pressurization based on the second trigger signal tr2 (a timing between local maximum points of displacements of the subject) is a timing calculated by dividing a time period between local maximum points of two successive displacements of the subject into two or more equal parts.

In addition, based on a displacement amount that was fed back from the displacement amount feedback circuit 33, the pressurization mechanism control circuit 32 controls a pressurization displacement amount that is applied to the subject by the first automatic pressurization mechanism 12 and a pressurization displacement amount that is applied to the subject by the second automatic pressurization mechanism 13 so that the displacement amount maintains a constant value.

In this case, for example, automatic control so that a displacement amount that is obtained from the displacement amount feedback circuit 33 as a result of pressurization by the first automatic pressurization mechanism 12 and the second automatic pressurization mechanism 13 approaches a target displacement amount may be mentioned as control that is performed by the pressurization mechanism control circuit 32 so that the displacement amount maintains a constant value. Similarly to the above described Embodiment 2, the target displacement amount may be a predetermined value or may be an input value that is inputted from outside. In this case, the displacement amount that is obtained from the displacement amount feedback circuit 33 is reflected in the control of both the first automatic pressurization mechanism 12 and the second automatic pressurization mechanism 13.

Further, automatic control so that a pressurization displacement amount that is caused by the second automatic pressurization mechanism 13 approaches a displacement amount that is obtained from the displacement amount feedback circuit 33 as a result of pressurization by the first automatic pressurization mechanism 12 may be mentioned as another control example. This control is control that makes an automatic pressurization displacement amount that is caused by the second automatic pressurization mechanism 13 that is indicated by alternate long and short dash line arrows in FIG. 10 approach a displacement amount obtained by adding an automatic pressurization displacement amount that is caused by the first automatic pressurization mechanism 12 and a spontaneous displacement amount of the subject that is indicated by solid line arrows in FIG. 10 (control that makes the former match the latter). In this case, a displacement amount obtained from the displacement amount feedback circuit 33 is reflected only in the control of the second automatic pressurization mechanism 13.

In addition, automatic control so that a displacement amount that is the result of pressurization by the first automatic pressurization mechanism 12 or the second automatic pressurization mechanism 13 that is performed the next time approaches a displacement amount obtained from the displacement amount feedback circuit 33 as a result of pressurization by the first automatic pressurization mechanism 12 or the second automatic pressurization mechanism 13 that was performed the previous time may be mentioned as a further example of another control. This control is control that, regardless of whether the displacement amount in question is a displacement amount obtained by adding a spontaneous displacement amount and a pressurization displacement amount or is a displacement amount that is caused by only a pressurization displacement, adjusts the displacement amount in an alternating manner so as to approach the displacement amount obtained the previous time. In this case also, the displacement amount that is obtained from the displacement amount feedback circuit 33 is reflected in the control of both the first automatic pressurization mechanism 12 and the second automatic pressurization mechanism 13.

Thus, the first automatic pressurization mechanism 12 and the second automatic pressurization mechanism 13 perform automatic pressurization by controlling a voltage applied to a circuit or the like so that the displacement amount maintains a constant value based on control of the pressurization mechanism control circuit 32.

Note that a signal that is based on a displacement of the subject is not limited to an electrocardiographic signal or a PW signal. For example, similarly to the respective embodiments described above, a configuration may also be adopted so as to determine not only the timing of the first trigger signal tr1 but also the timing of the second trigger signal tr2 using a displacement amount for an image (or alternatively, another signal) that is measured by the displacement measurement circuit for elasticity image generation 28.

According to Embodiment 3, in addition to obtaining substantially the same advantageous effects as in the above described Embodiments 1 and 2, it is possible to also acquire an elasticity image at a timing other than a timing of a spontaneous displacement of the subject, and thus elasticity images that show a smoother motion can be observed.

In addition, in the case of performing the automatic pressurization by the second automatic pressurization mechanism 13 at a time point calculated by dividing a time period between spontaneous displacements of the subject into equal parts, subject displacements that are at equal time intervals are obtained, and it is possible to obtain more preferable elasticity images.

Note that, although an ultrasound observation system has been mainly described in the foregoing description, the present invention may be an operation method that causes an ultrasound observation system to operate as described above, or a processing program for causing a computer to execute an operation method of an ultrasound observation system, or a non-transitory computer-readable storage medium that records the processing program or the like.

Further, the present invention is not limited to the precise embodiments described above, and can be embodied in the implementing stage by modifying the components without departing from the scope of the invention. Also, various aspects of the invention can be formed by appropriately combining a plurality of the components disclosed in the embodiments described above. For example, some components may be deleted from all of the disclosed components according to the embodiments. Furthermore, components from different embodiments may be appropriately combined. Thus, naturally various modifications and applications are possible within a range that does not deviate from the spirit and scope of the present invention.

What is claimed is:

1. An ultrasound observation system, comprising:
an ultrasound transducer that transmits ultrasound to a subject, receives the ultrasound that is reflected by the subject, and generates an ultrasound signal based on the ultrasound that is received;
a displacement measurement circuit that measures a displacement of the subject based on the ultrasound signal, in order to generate an elasticity image of the subject;
an elasticity modulus calculation circuit that calculates an elasticity modulus of the subject based on a measurement result of the displacement measurement circuit;

a pressurization mechanism comprising a pressurization face that applies a pressing force to the subject to generate a pressurization displacement;

a signal waveform analysis circuit that analyzes a periodic motion of the subject based on a waveform of a signal that is based on a spontaneous displacement of the subject; and a pressurization mechanism control circuit that, based on the periodic motion of the subject that is analyzed by the signal waveform analysis circuit, controls the pressurization mechanism so that the pressurization mechanism applies a pressing force to the subject and generates the pressurization displacement so as to reduce an influence of the spontaneous displacement of the subject at a time that the elasticity modulus is calculated by the elasticity modulus calculation circuit.

2. The ultrasound observation system according to claim 1, wherein:

the signal waveform analysis circuit analyzes a waveform of a signal that is based on the spontaneous displacement of the subject, and acquires an analysis result including a local maximum point of the spontaneous displacement and a displacement cycle; and based on the analysis result, the pressurization mechanism control circuit controls so as to cause the pressurization mechanism to perform pressurization at a timing that corresponds with the local maximum point of the spontaneous displacement in synchrony with the displacement cycle.

3. The ultrasound observation system according to claim 2, wherein the pressurization mechanism control circuit controls so as to cause the pressurization mechanism to perform pressurization at a same timing as the local maximum point of the spontaneous displacement.

4. The ultrasound observation system according to claim 3, further comprising:

a displacement amount feedback circuit that calculates a displacement amount of the subject based on the ultrasound signal and outputs the displacement amount, wherein the pressurization mechanism control circuit further controls a pressurization displacement amount applied to the subject, based on the displacement amount that is obtained from the displacement amount feedback circuit.

5. The ultrasound observation system according to claim 4, wherein, based on the periodic motion of the subject that is analyzed by the signal waveform analysis circuit, the pressurization mechanism control circuit generates a first trigger signal for causing the pressurization mechanism to perform pressurization at a same timing as the local maximum point of the spontaneous displacement, and a second trigger signal for causing the pressurization mechanism to perform pressurization at a timing that is between local maximum points of two of the spontaneous displacements that are successive.

6. The ultrasound observation system according to claim 5, wherein:

the pressurization mechanism comprises a first pressurization mechanism and a second pressurization mechanism; and the pressurization mechanism control circuit generates the first trigger signal for the first pressurization mechanism and generates the second trigger signal for the second pressurization mechanism based on the periodic motion of the subject that is analyzed by the signal waveform analysis circuit.

7. The ultrasound observation system according to claim 5, wherein the pressurization mechanism control circuit automatically controls so that a pressurization displacement amount caused by the second trigger signal approaches the displacement amount that is obtained from the displacement amount feedback circuit as a result of pressurization caused by the first trigger signal.

8. The ultrasound observation system according to claim 5, wherein the pressurization mechanism control circuit automatically controls so that a displacement amount that is a result of pressurization caused by the second trigger signal or the first trigger signal a next time approaches the displacement amount that is obtained from the displacement amount feedback circuit as a result of pressurization caused by the first trigger signal or the second trigger signal a previous time.

9. The ultrasound observation system according to claim 5, wherein the pressurization mechanism control circuit automatically controls so that the displacement amount that is obtained from the displacement amount feedback circuit as a result of pressurization caused by the first trigger signal and the second trigger signal approaches a target displacement amount.

10. The ultrasound observation system according to claim 4, wherein the pressurization mechanism control circuit automatically controls so that the displacement amount that is obtained from the displacement amount feedback circuit approaches a target displacement amount.

11. The ultrasound observation system according to claim 5, wherein the timing that is between local maximum points of the spontaneous displacements is a timing calculated by dividing a time period between local maximum points of two of the spontaneous displacements that are successive into two or more equal parts.

12. The ultrasound observation system according to claim 3, wherein the signal that is based on a spontaneous displacement of the subject is an electrocardiographic signal or a pulse-wave Doppler signal.

13. An operation method of an ultrasound observation system, wherein:

an ultrasound transducer transmits ultrasound to a subject, receives the ultrasound that is reflected by the subject, and generates an ultrasound signal based on the ultrasound that is received;

a displacement measurement circuit measures a displacement of the subject based on the ultrasound signal, in order to generate an elasticity image of the subject;

an elasticity modulus calculation circuit calculates an elasticity modulus of the subject based on a measurement result of the displacement measurement circuit;

a pressurization mechanism applies, through a pressurization face, a pressing force to the subject to generate a pressurization displacement;

a signal waveform analysis circuit analyzes a periodic motion of the subject based on a waveform of a signal that is based on a spontaneous displacement of the subject; and based on the periodic motion of the subject that is analyzed by the signal waveform analysis circuit, a pressurization mechanism control circuit controls the pressurization mechanism so that the pressurization mechanism applies a pressing force to the subject and generates the pressurization displacement so as to reduce an influence of the spontaneous displacement of the subject at a time that the elasticity modulus is calculated by the elasticity modulus calculation circuit.

14. The operation method of an ultrasound observation system according to claim 13, wherein:

the signal waveform analysis circuit analyzes a waveform of a signal that is based on the spontaneous displacement of the subject, and acquires an analysis result including a local maximum point of the spontaneous displacement and a displacement cycle; and based on the analysis result, the pressurization mechanism control circuit controls so as to cause the pressurization mechanism to perform pressurization at a timing that corresponds with the local maximum point of the spontaneous displacement in synchrony with the displacement cycle.

15. The operation method of an ultrasound observation system according to claim 14, wherein the pressurization mechanism control circuit controls so as to cause the pressurization mechanism to perform pressurization at a same timing as the local maximum point of the spontaneous displacement.

16. A non-transitory computer-readable storage medium storing a program that when executed by a computer causes the computer to perform an operation method of an ultrasound observation system, wherein the method comprises:

measuring a displacement of a subject based on an ultrasound signal, in order to generate an elasticity image of the subject, wherein the ultrasound signal is generated based on received ultrasound that is transmitted to and reflected by the subject;

calculating an elasticity modulus of the subject based on a measurement result of the displacement of the subject;

controlling a pressurization mechanism to apply, through a pressurization face, a pressing force to the subject to generate a pressurization displacement;

analyzing a periodic motion of the subject based on a waveform of a signal that is based on a spontaneous displacement of the subject; and based on the periodic motion of the subject, controlling the pressurization mechanism so that the pressurization mechanism applies a pressing force to the subject and generates the pressurization displacement so as to reduce an influence of the spontaneous displacement of the subject at a time that the elasticity modulus is calculated.

* * * * *